(12) United States Patent
Anderson

(10) Patent No.: US 11,341,252 B1
(45) Date of Patent: May 24, 2022

(54) PERSONAL INFORMATION SECURITY SYSTEM AND METHOD OF USE

(71) Applicant: Cody Ray Anderson, Paradise, TX (US)

(72) Inventor: Cody Ray Anderson, Paradise, TX (US)

( * ) Notice: Subject to any disclaimer, the term of this patent is extended or adjusted under 35 U.S.C. 154(b) by 0 days.

(21) Appl. No.: 16/299,495

(22) Filed: Mar. 12, 2019

(51) Int. Cl.
*G06F 21/60* (2013.01)
*H04L 9/08* (2006.01)
*G06F 21/62* (2013.01)
*G16H 10/60* (2018.01)

(52) U.S. Cl.
CPC .......... *G06F 21/602* (2013.01); *G06F 21/604* (2013.01); *G06F 21/6245* (2013.01); *H04L 9/088* (2013.01); *G16H 10/60* (2018.01)

(58) Field of Classification Search
CPC .. G06F 21/6245; G06F 21/604; G06F 21/602; H04L 9/088; G16H 10/60
See application file for complete search history.

(56) References Cited

U.S. PATENT DOCUMENTS

| 5,495,533 | A * | 2/1996 | Linehan | G06F 21/31 380/277 |
| 6,961,851 | B2 * | 11/2005 | Burritt | H04L 63/04 713/168 |
| 8,479,078 | B2 * | 7/2013 | Resch | G06F 11/1076 714/763 |
| 9,094,379 | B1 * | 7/2015 | Miller | H04L 9/0822 |
| 9,112,886 | B2 * | 8/2015 | Dodd | H04L 63/0428 |
| 11,075,754 | B2 * | 7/2021 | Brown | H04L 9/088 |
| 2005/0055560 | A1 * | 3/2005 | Kendon | G06F 21/6245 713/189 |
| 2008/0126357 | A1 * | 5/2008 | Casanova | G06F 16/1844 |
| 2011/0276350 | A1 * | 11/2011 | Khanal | G16H 10/65 705/3 |
| 2015/0310219 | A1 * | 10/2015 | Haager | H04L 9/0894 713/165 |
| 2016/0085996 | A1 * | 3/2016 | Eigner | G06F 21/6227 713/193 |
| 2017/0061138 | A1 * | 3/2017 | Lambert | H04L 63/0428 |
| 2019/0081782 | A1 * | 3/2019 | Dewitt | G06F 21/78 |
| 2019/0087541 | A1 * | 3/2019 | Kubota | G16H 10/60 |
| 2019/0147137 | A1 * | 5/2019 | Gergely | H04L 9/3239 705/51 |

* cited by examiner

*Primary Examiner* — Ali S Abyaneh

(74) *Attorney, Agent, or Firm* — Leavitt Eldredge Law Firm

(57) ABSTRACT

A personal information security system allows for the storage of data in a secure manner by assigning a key to the data and breaking up the data then sending parts or pieces to many computing devices on a network. The data is requested and gathered from the user base by providing the key to the data.

1 Claim, 6 Drawing Sheets

PERSONAL INFORMATION SECURITY SYSTEM AND METHOD OF USE

BACKGROUND

1. Field of the Invention

The present invention relates generally to security systems, and more specifically, to a personal information security system for gathering, storing and disseminating confidential data without loss or theft.

2. Description of Related Art

Security systems are well known in the art and are effective means to limit the exposure or risk of an individual or property to harm, loss or theft. For example, FIG. 1 depicts a conventional information system 101 having a person 103 with data 105 and locations such as a medical office 107, a financial institution 109 and a retail store 111. The person 103 frequents the locations to use their service, the medical office 107 keeps patient records and requires payment, the financial institution 109 keeps and transfers data to enable monetary transfers, and the retail store 111 requires payment and in online cases retains login and order history data. Good or services from the locations are available to the person 103.

One of the problems commonly associated with system 101 is limited efficiency. For example, each location must ensure that any personal data 105 that is stored or passes through it remains secure and is an opportunity for that data 105 to be stolen or lost.

Accordingly, although great strides have been made in the area of information systems, many shortcomings remain.

DESCRIPTION OF THE DRAWINGS

The novel features believed characteristic of the embodiments of the present application are set forth in the appended claims. However, the embodiments themselves, as well as a preferred mode of use, and further objectives and advantages thereof, will best be understood by reference to the following detailed description when read in conjunction with the accompanying drawings, wherein:

Figure 1:
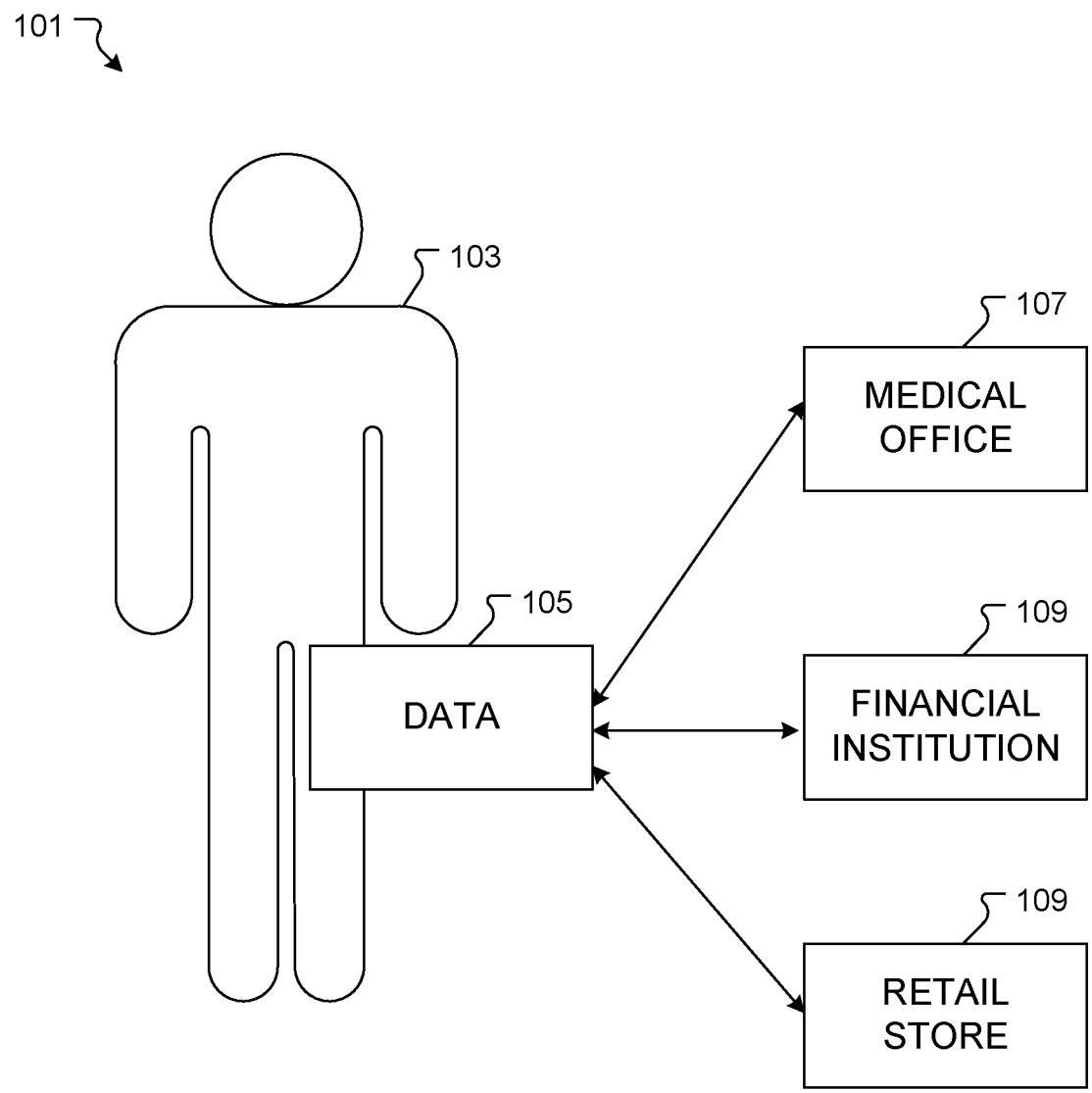
FIG. 1 is a diagram of a common information system.

While the system and method of use of the present application is susceptible to various modifications and alternative forms, specific embodiments thereof have been shown by way of example in the drawings and are herein described in detail. It should be understood, however, that the description herein of specific embodiments is not intended to limit the invention to the particular embodiment disclosed, but on the contrary, the intention is to cover all modifications, equivalents, and alternatives falling within the spirit and scope of the present application as defined by the appended claims.

DETAILED DESCRIPTION OF THE PREFERRED EMBODIMENT

Illustrative embodiments of the system and method of use of the present application are provided below. It will of course be appreciated that in the development of any actual embodiment, numerous implementation-specific decisions will be made to achieve the developer's specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure.

The system and method of use in accordance with the present application overcomes one or more of the above-discussed problems commonly associated with conventional information systems. Specifically, the invention of the present application reduces the burden on institutions to keep and maintain data in secure manner. These and other unique features of the system and method of use are discussed below and illustrated in the accompanying drawings.

The system and method of use will be understood, both as to its structure and operation, from the accompanying drawings, taken in conjunction with the accompanying description. Several embodiments of the system are presented herein. It should be understood that various components, parts, and features of the different embodiments may be combined together and/or interchanged with one another, all of which are within the scope of the present application, even though not all variations and particular embodiments are shown in the drawings. It should also be understood that the mixing and matching of features, elements, and/or functions between various embodiments is expressly contemplated herein so that one of ordinary skill in the art would appreciate from this disclosure that the features, elements, and/or functions of one embodiment may be incorporated into another embodiment as appropriate, unless described otherwise.

The preferred embodiment herein described is not intended to be exhaustive or to limit the invention to the precise form disclosed. It is chosen and described to explain the principles of the invention and its application and practical use to enable others skilled in the art to follow its teachings.

Figure 2:
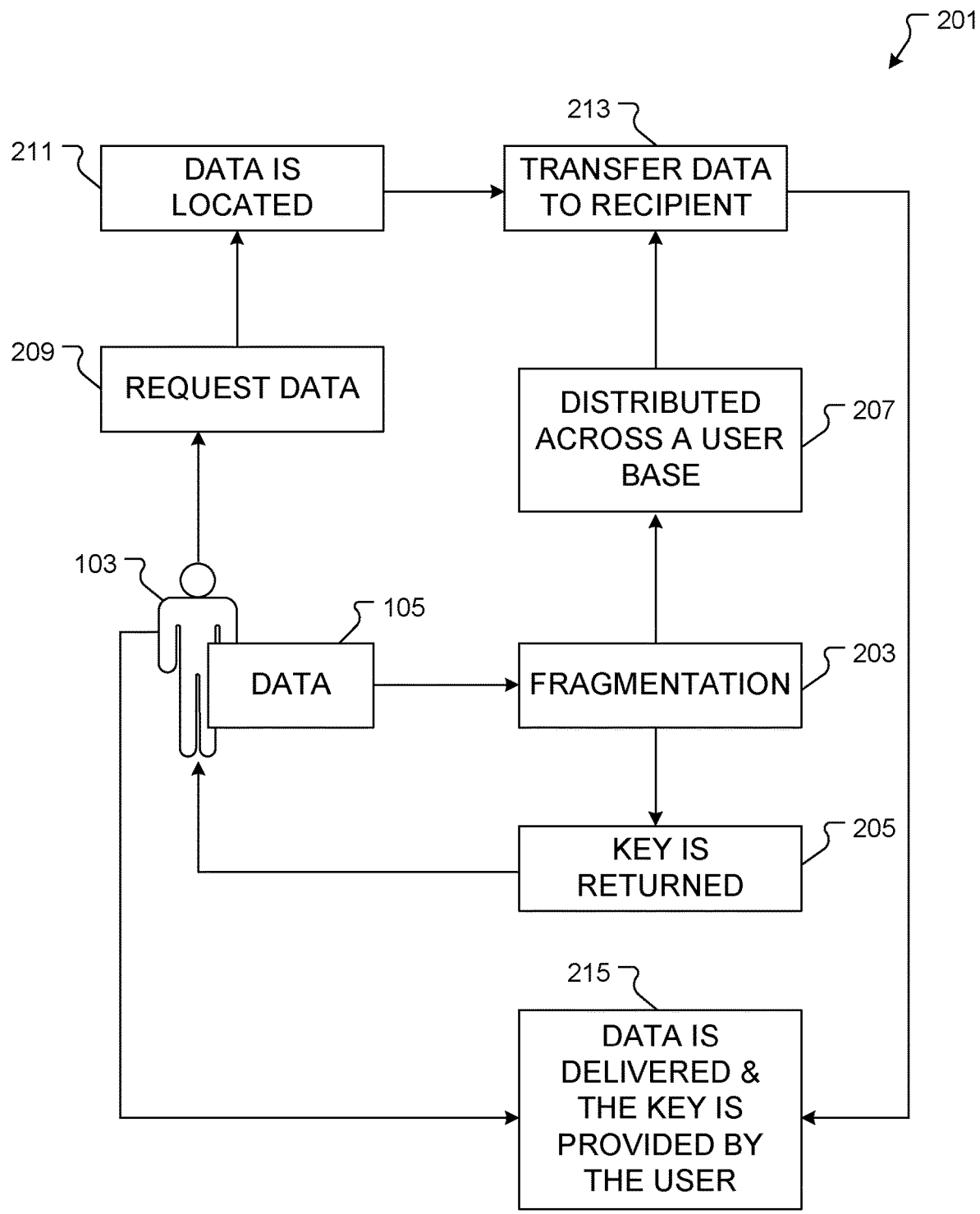
FIG. 2 is a flowchart of a personal information security system in accordance with a preferred embodiment of the present application.

Referring now to the drawings wherein like reference characters identify corresponding or similar elements throughout the several views, FIG. 2 depicts a flowchart of a personal information system in accordance with a preferred embodiment of the present application. It will be appreciated that system 201 overcomes one or more of the above-listed problems commonly associated with conventional information systems.

In the contemplated embodiment, system 201 includes the data 105 of a user 103 that is stored in an electronic format. That data 105 is fragmented 203 with a key that is required to reconstitute the data 105. The key is returned 103 to the user 205 and the data is distributed over a userbase 207. It is contemplated that the user base could have any number of computing devices so long as they are configured to receive and store the fragmented data.

In use, the user 103 requests the data 105, the data is then located 211 and transferred to the intended recipient 203. After the data is delivered it is reconstituted with the key provided by the user 215.

It should be appreciated that one of the unique features believed characteristic of the present application is that any requester that has need of the data 105 does not need to worry about storing and keeping the data safe when not in use.

Figure 3:
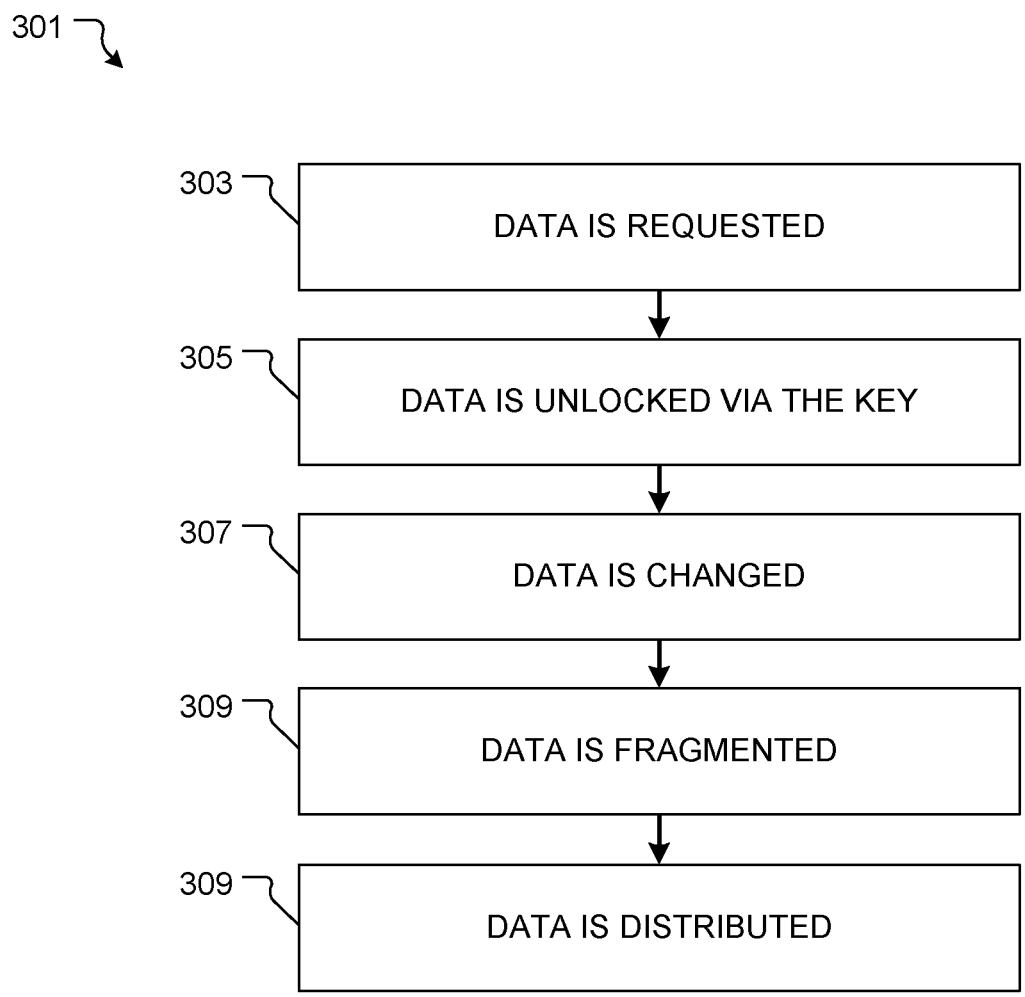
FIG. 3 is a flowchart of an alternative embodiment of the system of FIG. 2.

It is contemplated and will be appreciated that the data 105 is dynamic and that it could therefor be amended and re-fragmented as depicted by FIG. 3. The alternative embodiment 301 of system 201 includes similar features as that of system 201 wherein after the data is requested 303 and unlocked via the key 305 the data is changed 307 such as adding data thereto, removing data or other such operations, the data is fragmented 309 anew and distributed 309 across the user base.

Figure 4:
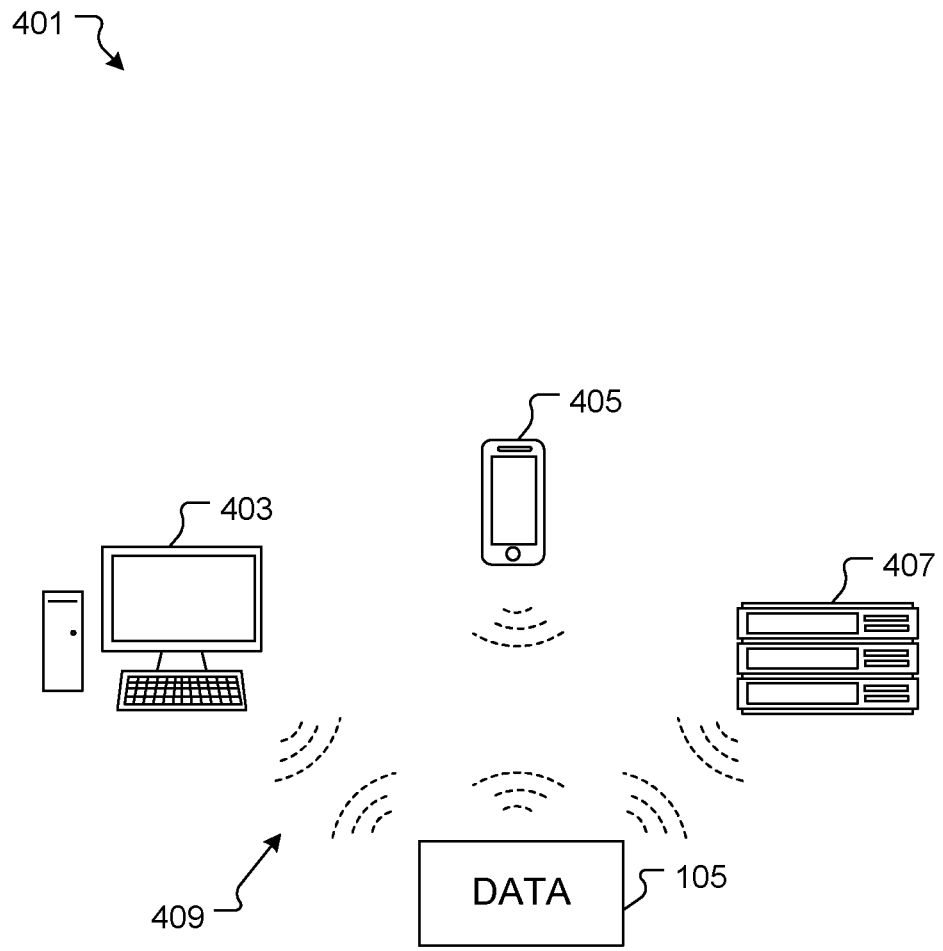
FIG. 4 is a diagram of the user base of FIG. 2.

Referring now to FIG. 4 the user base of system 201 is depicted. It is contemplated that the user base 401 includes a network 409 of computing devices. It is contemplated that personal computing devices 403 such as home computers, portable computing devices 405 such as smart phones or industrial computing devices 407 such as servers, all collaborate together to store data 105 thereon. It will be appreciated that any computing devices including those under development and those that will be developed in the future could be used as part of the user base.

Figure 5:
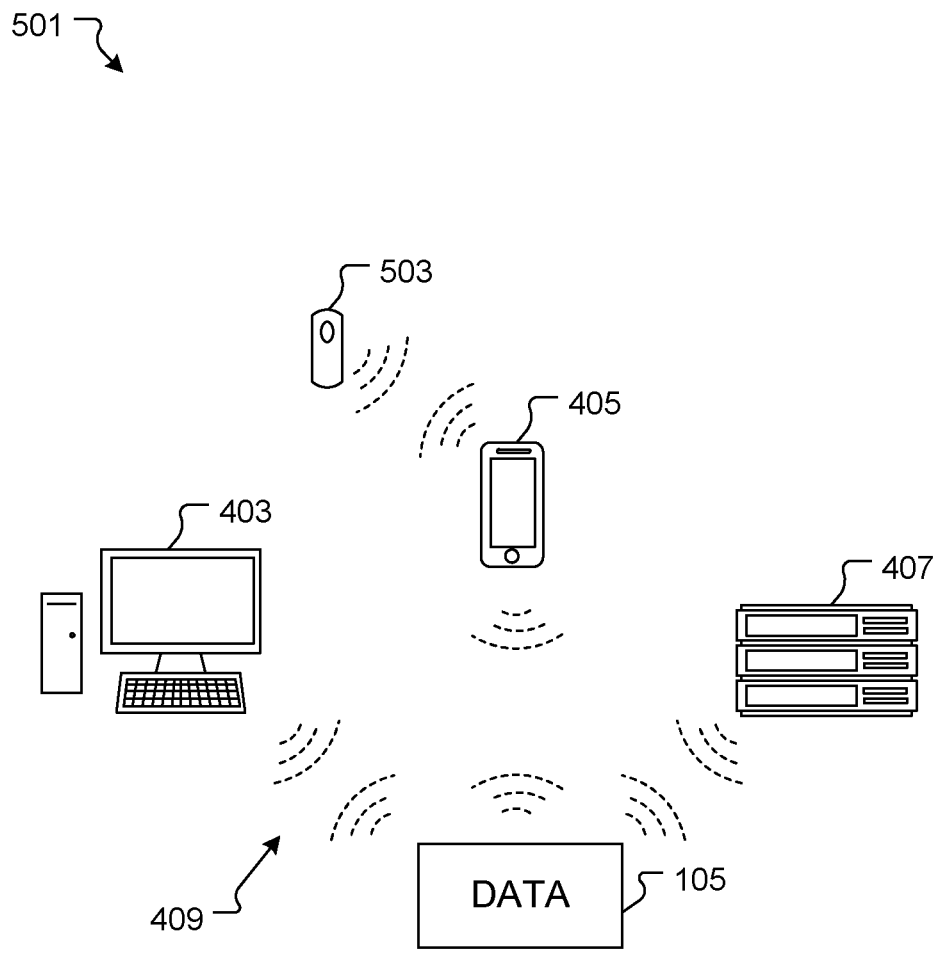
FIG. 5 is a diagram of an alternative embodiment of the system of FIG. 2.

It is contemplated that the key 305 could become lost or destroyed potentially limiting the use of the system 201. Referring now to FIG. 5 an alternative embodiment of the system 201 is depicted. Embodiment 501 includes similar features as system 201 and user base 401 wherein a master decryption device 503 is in electronic communication with at least one of the computing devices of the user base such as the portable computing device 405. It is contemplated that the master decryption device 503 is configured to determine the key 305 when it has been lost or corrupted to restore access to the data 105 protected by the key 305.

Figure 6:
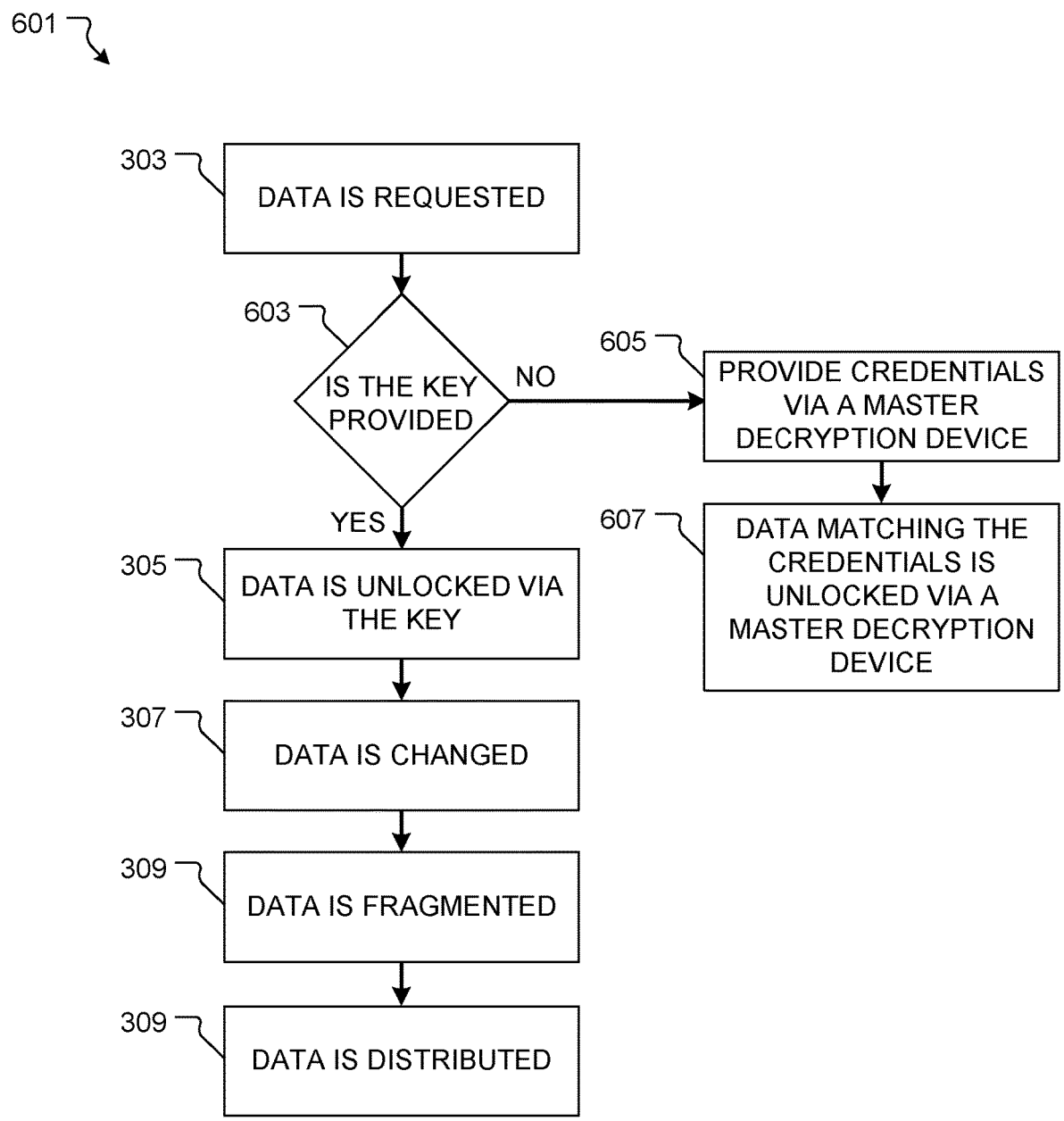
FIG. 6 is a flowchart of an alternative method of use of the system of FIG. 5.

Referring now to FIG. 6 an alternative method of use of the system 501 is depicted. Method 601 includes similar steps as method 301 wherein the presence of a key is determined 603, if no key is rendered, providing credentials via a master decryption device 605 and unlocking data that corresponding to the credentials is unlocked via a master decryption device 607. It is contemplated that the data stored within the system could be classified and that data such as blood type, medicine allergies or the like could be categorized as, 'available to medical professionals.' Should the person not be conscious or the key unavailable to unlock the data, the data becomes available to the medical professional via a master decryption device.

The particular embodiments disclosed above are illustrative only, as the embodiments may be modified and practiced in different but equivalent manners apparent to those skilled in the art having the benefit of the teachings herein. It is therefore evident that the particular embodiments disclosed above may be altered or modified, and all such variations are considered within the scope and spirit of the application. Accordingly, the protection sought herein is as set forth in the description. Although the present embodiments are shown above, they are not limited to just these embodiments, but are amenable to various changes and modifications without departing from the spirit thereof.

What is claimed:

1. A method of storing and accessing data, consisting of:
   providing a plurality of computing devices in communication via an electronic network;
   providing a master decryption device in data communication with the plurality of computing device;
   submitting data by a submitter, the data being personal information about a user;
      fragmenting the data into a plurality of randomly sized fragments, wherein each of the plurality of fragments is unusable by itself;
   creating a single key specifically for the user;
   sending the single key to the submitter;
   distributing the plurality of fragments over a user base, the user base consisting of the plurality of computing devices;
   requesting the data by the user;
   determining if the single key is provided by the user;
   when the single key is provided by the user, reconstituting the plurality of fragments through use of the single key, wherein the single key directs the reconstituting;
      accessing the data after the plurality of fragments are reconstituted into the data, from one of the plurality of computing devices;
      changing the data by removing or adding to the data;
      re-fragmenting the data into a second plurality of fragments; and
      re-distributing the second plurality of fragments over the user base;
   when the single key is not provided by the user, using the master decryption device to provide credentials; and
      wherein the data is retrieved and reconstituted from the user base based on matching the credential via a master decryption device.

* * * * *